United States Patent
Greter et al.

(10) Patent No.: US 9,981,283 B2
(45) Date of Patent: *May 29, 2018

(54) DISCHARGE DEVICE FOR PASTE-LIKE MATERIALS WITH SEPARATELY FORMED ADAPTER FOR CONNECTING A CONTAINER TO A BASE BODY

(71) Applicant: MEDMIX SYSTEMS AG, Rotkreuz (CH)

(72) Inventors: Andy Greter, Rotkreuz (CH); Beat Mathys, Zufikon (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/391,150

(22) Filed: Dec. 27, 2016

(65) Prior Publication Data

US 2017/0173624 A1 Jun. 22, 2017

Related U.S. Application Data

(62) Division of application No. 14/355,469, filed as application No. PCT/CH2012/000228 on Oct. 1, 2012, now Pat. No. 9,566,102.

(30) Foreign Application Priority Data

Nov. 1, 2011 (CH) ........................ 1758/11

(51) Int. Cl.
*B65D 88/54* (2006.01)
*G01F 11/00* (2006.01)
(Continued)

(52) U.S. Cl.
CPC .... *B05C 17/00596* (2013.01); *A61B 17/8805* (2013.01); *A61B 17/8833* (2013.01);
(Continued)

(58) Field of Classification Search
CPC ............ A61B 17/8805; A61B 17/8833; B05C 17/00519; B05C 17/00596;
(Continued)

(56) References Cited

U.S. PATENT DOCUMENTS 963,840 A * 7/1910 Whitaker ................ F16N 37/02
206/384
1,783,683 A 12/1928 Tomlison
(Continued)

FOREIGN PATENT DOCUMENTS

| CH | 641 736 A5 | 3/1984 |
| CN | 2661117 Y | 12/2004 |

(Continued)

OTHER PUBLICATIONS

International Search Report of PCT/CH2012/000228, dated Aug. 1, 2013.

(Continued)

*Primary Examiner* — Benjamin R Shaw
(74) *Attorney, Agent, or Firm* — Sughrue Mion, PLLC

(57) ABSTRACT

This invention relates to a discharge device of the dispenser gun type, which is suitable in particular for discharging semi-solid materials such as e.g. bone replacement materials. The discharge device comprises an adapter (400) which is removably attached to a main body (110) of the discharge device. A fastening structure for attachment of a container (300) is formed on the adapter substantially along a proximal direction (C) contrary to the feed direction (A). As a result various types of containers can be fastened to the machine without the need to change the mechanism of the device. The container can be provided on both ends with identical external threads and can be closed by closure caps in order to enable intuitive handling. In order to improve access to points which are difficult to reach, the container (Continued)

may be in the form of a curved pipe or may be formed flexibly. The piston rod (200) of the discharge device is then also formed flexibly.

18 Claims, 4 Drawing Sheets

(51) Int. Cl.
| | | |
|---|---|---|
| *B05C 17/005* | (2006.01) | |
| *A61B 17/88* | (2006.01) | |
| *B05C 17/01* | (2006.01) | |
| *B65D 83/00* | (2006.01) | |
| *A61C 5/62* | (2017.01) | |

(52) U.S. Cl.
CPC .......... *A61C 5/62* (2017.02); *B05C 17/00513* (2013.01); *B05C 17/0113* (2013.01); *B05C 17/0123* (2013.01); *B65D 83/0033* (2013.01)

(58) Field of Classification Search
CPC . B05C 17/0123; B05C 17/01; B05C 17/0113; A61C 5/62; B65D 83/0033; B05B 11/0054; G01F 11/026; A61M 2005/31518; A61M 5/3129; A61M 5/31581
USPC ................. 222/326, 325, 386–391, 526–527
See application file for complete search history.

(56) References Cited

U.S. PATENT DOCUMENTS

| | | | |
|---|---|---|---|
| 2,102,939 A | | 7/1936 | Bishop |
| 2,340,433 A | * | 2/1944 | Skinner .................... B05C 17/01 222/391 |
| 2,461,211 A | * | 2/1949 | Guthrie .............. B65D 83/0044 211/65 |
| 3,076,225 A | * | 2/1963 | Sherbondy .......... B05C 17/0123 222/323 |
| 3,341,085 A | * | 9/1967 | Sundholm ................. F16N 3/12 222/260 |
| 4,090,639 A | * | 5/1978 | Campbell ........... B05C 17/0123 222/309 |
| 4,330,070 A | * | 5/1982 | Doubleday ............. B05C 17/01 222/287 |
| 4,339,058 A | * | 7/1982 | Wendt .................... B05C 17/01 222/309 |
| 4,738,664 A | | 4/1988 | Prindle |
| 4,744,494 A | | 5/1988 | Seager et al. |
| 5,005,735 A | * | 4/1991 | Keller ............... B05C 17/00553 222/137 |
| 5,137,131 A | | 8/1992 | Enomoto |
| 5,370,271 A | * | 12/1994 | Segatz ............. B05C 17/00583 222/105 |
| 5,464,131 A | | 11/1995 | Keller |
| 5,526,960 A | * | 6/1996 | Breidenbach .......... A45D 34/02 222/183 |
| 5,692,642 A | | 12/1997 | Brattesani |
| 5,735,437 A | | 4/1998 | Broyles et al. |
| 5,743,431 A | | 4/1998 | Brattesani |
| 5,823,403 A | * | 10/1998 | Schneider ............... B05C 17/01 222/391 |
| 5,992,694 A | | 11/1999 | Keller |
| 6,395,006 B1 | * | 5/2002 | Burchett ............ A61B 17/8816 606/92 |
| 7,118,378 B1 | * | 10/2006 | Karapetyan .......... A61C 8/0009 433/90 |
| 8,424,727 B2 | * | 4/2013 | Herman ................ G01F 11/026 222/105 |
| 9,297,498 B1 | * | 3/2016 | Kuntzelman ............. F16N 3/12 |
| 2002/0004651 A1 | * | 1/2002 | Ljunggreen ....... A61M 5/31501 604/218 |
| 2005/0070912 A1 | | 3/2005 | Voellmicke |
| 2007/0289998 A1 | * | 12/2007 | Keller ............... B05C 17/00553 222/137 |
| 2008/0172058 A1 | * | 7/2008 | Trieu ..................... A61B 17/70 606/94 |
| 2009/0255960 A1 | | 10/2009 | Keller |
| 2011/0218513 A1 | | 9/2011 | Walker et al. |
| 2013/0034830 A1 | * | 2/2013 | Song .................... A61C 8/0006 433/90 |

FOREIGN PATENT DOCUMENTS

| | | |
|---|---|---|
| CN | 101462099 A | 6/2009 |
| DE | 8901554 U1 | 6/1989 |
| DE | 298 21 422 U1 | 3/1999 |
| EP | 0 412 198 A1 | 2/1991 |
| EP | 1 247 746 A1 | 10/2002 |
| GB | 879272 A | 10/1961 |
| WO | 2005/008819 A2 | 1/2005 |
| WO | 2011/009221 A1 | 1/2011 |

OTHER PUBLICATIONS

Communication, dated Sep. 25, 2015 from the State Intellectual Property Office of the People's Republic of China in counterpart application No. 201280054203.8.
Communication dated Aug. 29, 2017, from European Patent Office in counterpart application No. 17153370.6.

* cited by examiner

DISCHARGE DEVICE FOR PASTE-LIKE MATERIALS WITH SEPARATELY FORMED ADAPTER FOR CONNECTING A CONTAINER TO A BASE BODY

This is a Divisional of application Ser. No. 14/355,469 filed Apr. 30, 2014, claiming priority based on International Application No. PCT/CH2012/000228 filed Oct. 1, 2012, claiming priority based on Swiss Patent Application No. 01758/11, filed Nov. 1, 2011, the contents of all of which are incorporated herein by reference in their entirety.

TECHNICAL FIELD

The present invention relates to a discharge device and to a container for use with such a discharge device. The discharge device according to the invention is suitable, in particular, for discharging semi-solid materials such as cements (in particular bone cements or dental cements) or artificial bone graft substitute materials, but also for other types of flowable materials, in particular for all types of highly viscous, paste-like materials.

PRIOR ART

For discharging highly viscous fluids, so-called dispenser guns are known. Such a dispenser normally comprises a base body on which a cartridge or syringe with liquid contained therein is held. A rigid handgrip and a pivotable operating lever are connected to the base body. A piston rod extends through the base body. When a user pulls the operating lever from its home position in the direction of the handgrip, the piston rod is advanced in a distal direction relative to the base body. In this arrangement the force transmission between the operating lever and the piston rod can take place directly or indirectly. The operating lever is spring loaded in such a manner that when it is no longer held it returns into its home position. With renewed operation of the operating lever a further feed of the piston rod occurs.

From US 2007/0289998 A1 a discharge device is known in which a multi-component syringe or multi-component cartridge with its holding flange can be laterally slid into a syringe retaining device. In this device it is possible, depending on the type and size of the syringe, to manufacture a different syringe retaining device. In this arrangement the syringe retaining devices can be exchangeable if need be. The device is suitable for specially matching multi-component syringes with a matching retaining flange, but not for other types of containers that do not have a retaining flange.

For discharging synthetic bone graft substitute materials it is known to pack such materials into a cylindrical pipe that comprises a substantially constant interior diameter and that, in particular, does not taper off at its outlet end. In this way excessive counterpressure and blockages during discharge can be prevented. Furthermore, it has been proposed to discharge bone graft substitute materials from such a pipe with a dispenser gun. Such a system is, for example, sold by Baxter International Inc. under the name of Actifuse™ MIS system. At its proximal end the pipe comprises a bayonet connection and is closed by means of a slidable piston, while at its distal end the pipe is closed by means of a slide-on cap. In order to administer the bone graft substitute material a surgeon fastens the pipe over the bayonet connection to the dispenser and removes the cap from the distal end. Handling such a system is not particularly intuitive to the surgeon. Since in the known system the pipe measures more than 20 cm in length, with such a system it may furthermore be difficult for the surgeon to reach positions that are difficult to access.

SUMMARY OF THE INVENTION

In a first aspect it is an object of the present invention to provide a discharge device that makes it possible in a simple manner to connect various containers to the discharge device without there being any need to change the mechanism of the device.

Thus a discharge device is provided that comprises a base body, an operating lever that is manually pivotable relative to the base body, and a piston rod that is slidable relative to the base body. The piston rod is coupled to the operating lever in such a manner that operating the operating lever causes advancing of the piston rod in a distal feed direction. In order to be able in a simple manner to connect various containers the discharge device comprises an adapter that is formed separately from the base body, that is fastened to the base body, and on which a fastening structure for attachment of a container substantially along a proximal direction contrary to the feed direction is arranged.

Unlike the device according to US 2007/0289998, such a device makes it possible to connect to the discharge device other types of containers that in contrast to syringes do not comprise a retaining flange. In particular, this device makes it possible to connect a container substantially contrary to the feed direction, e.g. by way of a screw connection, bayonet connection or axial snap-lock connection. To this effect the fastening structure can, for example, be a screw connection or bayonet connection that is open in the feed direction, or a corresponding snap-lock receiving device for the container.

The container to be connected can be a container in the form of a (straight or curved) cylindrical pipe with a substantially constant interior diameter, as will be described in more detail below. However, entirely different types of containers can be connected, which, if needed, can be tapered off at the distal end. The container to be connected is preferably a single container with a single reservoir in which a piston is slidable, on which in turn the piston rod acts; in other words, it is not a multi-compartment container with several reservoirs arranged in parallel. However, the use of such a device with multi-compartment containers is not excluded.

Preferably the device is in the form of a dispenser gun, i.e. it comprises a handgrip that is rigidly made in one piece with or affixed to the base body, with the operating lever being moved towards the handgrip in order to advance the piston rod. In particular embodiments, to this effect the handgrip is held with one hand of a user, and the operating lever is pulled, with the fingers of the same hand, towards the handgrip substantially contrary to the feed direction of the piston rod. To this effect the operating lever, near its upper or lower end, can be pivotably connected to the handgrip, or it can be movable towards the handgrip by being linearly displaced. Dispenser guns are known in a multitude of designs from the state of the art, and the present invention is in no way limited to a particular type of dispenser gun. For example, reference is made to the documents U.S. Pat. No. 5,137,181, U.S. Pat. No. 5,464,131, U.S. Pat. No. 5,992,694, US 2007/0289998 or WO 2011/009221, each of them showing a dispenser gun whose mechanical design can be used for transmitting movement from the operating lever to the piston rod in the context of the present invention. However, other designs of dispensers can also be used in which a lever produces a feed movement of a piston rod, e.g. dispensers in which the movable lever is moved towards the hand grip by the ball of the user's thumb, as shown, for example, in U.S. Pat. No. 4,744,494 or CH 641 736, or pen-type dispensers as in U.S. Pat. No. 5,735,437 or WO 2005/084819.

Preferably the adapter is removably attached to the base body. In order to be easily mountable, said adapter can preferably be inserted into the base body along a direction of insertion that extends across the feed direction. In particular it is preferred if the adapter can be laterally inserted into the base body, i.e. the direction of insertion preferably extends across a plane defined by the piston rod and the operating lever, or by the handgrip and the operating lever. However, the adapter can also, for example, be insertable from the top into the base body. In this context in the present document the term "across" is to be interpreted as follows: a direction extends "across" another direction if the angle between the directions is between 45° and 135°, preferably between 60° and 120°, in particular between 75° and 105°, and preferably approximately 90°.

The adapter can, in particular, be shaped as follows: it can comprise a main section with an axial passage opening for the piston rod, a fastening structure on the main section for the container, which fastening structure preferably extends at least partly around the passage opening (e.g. a threaded bushing that extends around the passage opening, or a bayonet mounting) as well as two opposing retaining wings that substantially extend in opposite lateral directions. In this arrangement the shape of the base body and of the retaining wings can substantially correspond to the shape of the proximal end of a syringe container that is known per se, i.e. the adapter can be slidable into a base body that per se is designed to receive a (single-compartment or multi-compartment) syringe. By assuming the shape of a syringe, the adapter makes it possible to use a dispenser, which per se is designed for use with syringes, also with other types of containers. In this case the base body of the discharge device will comprise an insertion opening, which is complementary to the adapter, with two opposite slits that extend across the feed direction and across the direction of insertion, for accommodating the retaining wings. In particular, the insertion opening can be designed as in the already-mentioned US 2007/0289998.

The base body can, in particular, comprise a housing and a separately manufactured retaining element that is connected to the housing and that is, in particular, removable, wherein the adapter is then attached to the retaining element. In this case it is thus not only the adapter that can easily be replaced by some other adapter, but also the retaining element, which serves to connect the adapter to the base body, that can easily be exchanged, during manufacture or subsequently, for some other retaining element. This provides even greater flexibility in the type of containers to be connected. Thus without any design changes in the lever mechanism it is possible to implement, for example, dispensers for various sizes of syringes (which are directly connected to the retaining element) and for various types of screw containers (for which in each case an adapter is provided for insertion into a particular retaining element). Since the lever mechanism, which is elaborate from the point of view of design, is always identical for all these dispensers, a whole series of dispensers can be created in the manner of a modular system in which the most cost-intensive components are always of identical design and thus can be produced economically in large numbers.

The retaining element can again be slidable into the housing along a fastening direction that extends across the feed direction. In this arrangement the fastening direction can be identical to the direction of insertion for the adapter, or it can, for example, extend across said direction of insertion.

Preferably, the adapter can be exchanged without there being a need to completely remove the piston rod from the base body. The adapter is thus preferably removable from the base body while the piston rod is held on the base body. This facilitates replacing the adapter. In contrast to this, the syringe retaining device of US 2007/0289998 is exchangeable only after the piston rod has been completely removed.

In a second aspect it is an object of the present invention to provide a container for semi-solid or viscous materials, which container can be used with a discharge device of the type mentioned above and allows particularly simple and intuitive handling.

Thus a container for use with a discharge device is provided, wherein the container contains a highly-viscous or semi-solid material that is preferably implantable, e.g. a synthetic bone graft substitute. The container has the shape of a cylindrical pipe that along its entire length has a substantially constant cross-sectional area (and thus a constant interior diameter) and that at each of its two ends comprises an external connecting structure. In this arrangement the connecting structures at each end are of the same design. Consequently it is possible to fasten either end of the container to the discharge device. Preferably, the connecting structures at each end are substantially identical. In this manner particularly intuitive handling is ensured. Moreover, the container is preferably at each end closed by means of a closure cap that engages the connecting structures. The closure caps are preferably substantially identical.

In particular, external threads can be provided on both ends. In this case, preferably, a closure cap with an internal thread is removably screwed onto each end. This ensures a tight seal. However, it is also possible to provide on both ends other types of connecting structures, e.g. external studs, external webs and/or external grooves for a bayonet connection. In this case, too, a corresponding closure cap of a complementary design can be attached to each end. If there are external threads, they preferably have identical parameters at each end of the container, in particular the number of threads, flank shape, external diameter, core diameter and thread pitch. Preferably the threads, and preferably also the closure caps, are in addition also identical in every other respect (in particular also comprising the same length). In this way it is immediately evident to a user that the orientation of the container is immaterial. Attachment of the container thus becomes particularly intuitive. This facilitates the work of the user (normally a surgeon) and reduces the risk of operator error. This can be an important factor in particular in the hectic atmosphere of an operating theatre. The same also applies to other types of connecting structures and closure caps.

Preferably, prior to removing the closure caps for the first time the container does not yet comprise a slidable piston, in other words in this case the piston is provided only by the discharge device. This reduces the danger of the piston sticking as a result of prolonged storage in the container, but it also provides the possibility of connecting the container in any desired orientation to the discharge device.

Preferably, the container is of a length that is at least five times, preferably at least ten times, particularly preferably at least twenty times the interior diameter. In absolute numbers the length of the pipe is preferably at least 100 mm, preferably approx. 150-300 mm. The interior diameter of the pipe is preferably approx. 3-10 mm, particularly preferably approx. 5-7 mm. The wall thickness of the pipe is preferably approx. 0.5-1 mm. The pipe can e.g. be made of polypropylene (PP), polyamide (PA), polyetheretherketone (PEEK) or polycarbonate (PC), while the closure caps can be made from the same material or from some other material.

The container can not just form a straight pipe; instead, it can also have the shape of a curved pipe so that its distal end encompasses an angle of at least 15°, preferably at least 30° or even 45° with the proximal end, or can be flexible in such a manner that its distal end is pivotable relative to the proximal end, in particular pivotable on an angle of at least 45°.

This makes it possible to reach even locations that are difficult to access. A flexible container can, for example, be manufactured from a flexible polyethylene (PE), from PP or from polytetrafluoroethylene (PTFE). If the container is flexible, it is preferred if the bending moment is less than 2.0 Nm, particularly preferably less than 1.0 Nm, particularly preferably less than 0.5 Nm, or even less than 0.1 Nm when the container is bent to a radius of curvature of 100 mm.

A corresponding discharge device for such a container again comprises a base body, an operating lever that is manually pivotable relative to the base body, and a piston rod that is slidable relative to the base body, wherein the piston rod is coupled to the operating lever in such a manner that operation of the operating lever causes the piston rod to advance in a distal feed direction. The base body then comprises a fastening structure that is complementary to the connecting structures of the container. If the connecting structures are, for example, external threads, the fastening structure on the base body comprises an internal thread. In contrast to this, if the connecting structures are, for example, elements of a bayonet connection such as bayonet studs, the fastening structure comprises a corresponding complementary bayonet mounting. The fastening structure can, in particular, be designed on an adapter that is formed separately from the base body and is preferably removably attached to the base body. In this regard reference is made to the above explanations relating to the discharge device with the adapter, which discharge device in every respect can be combined with a container of the type presently presented.

In a third aspect it is an object of the present invention to provide a discharge device that during application of the content allows better access to positions that are difficult to access.

Thus, again, a discharge device is provided that comprises a base body, an operating lever that is manually pivotable relative to the base body, and a piston rod that is slidable relative to the base body, wherein the piston rod is coupled to the operating lever in such a manner that operation of the operating lever causes the piston rod to advance in a distal feed direction. In order to render the device useable also with curved or flexible containers, for example the curved or flexible containers described above, and thus to improve access to positions that are difficult to access, the piston rod is flexible such that its distal end is flexible by an angle of at least 45°, preferably at least 60°, further preferably at least 90°, particularly preferably at least 135°, or even at least 180° relative to its proximal end, without the piston rod breaking.

In this arrangement flexing can be possible along a single bending direction, or the piston rod can even be flexible in two or more bending directions. The piston rod is designed such that the bending moment along at least one direction is preferably less than 2.0 Nm, particularly preferably less than 1.0 Nm, particularly preferably less than 0.5 Nm, or even less than 0.1 Nm when the piston rode is bent to a radius of curvature of 100 mm.

In order to improve its flexibility, the piston rod can comprise a first side on which there is a multitude of teeth regularly spaced apart from each other, wherein the operating lever when operated exerts a feed force directly or indirectly on the teeth in order to cause feed of the piston rod, and wherein the piston rod at least on a second side, which is opposite to the first lateral side, comprises a multitude of incisions in order to improve the flexibility of the piston rod. The incisions can be straight or, for example, wedge-shaped. They can be spaced apart from each other by a space that corresponds to the tooth spacing or to a multiple thereof. Preferably, in each case there is an incision opposite to a tooth base so that in this region the material thickness is reduced from both sides. In this design the material thickness can be limited to such an extent that an actual film hinge is formed between adjacent teeth. In addition, such incisions could also be provided on further sides of the piston rod, e.g. on those sides that are arranged so as to be offset on the feed axis by 90° relative to the teeth. Of course, completely different designs of the piston rod are also possible. For example it is also possible for the piston rod to comprise fully-fledged joints.

Such a device is preferably used together with a container in the form of a cylindrical pipe that is curved so that its distal end encompasses an angle of at least 15°, preferably at least 30°, or even 45° with the proximal end, or which pipe is flexible to such an extent that its distal end is pivotable by an angle of at least 45° relative to the proximal end. In this arrangement the length of the piston rod and of the pipe are selected in such a way that the piston rod in the container can substantially be advanced to the distal end of the container. In terms of the further characteristics such as flexibility, selection of materials etc. analogously the above-mentioned considerations relating to the container according to the invention apply, even in cases where the container used has no connecting structures or has connecting structures that differ from those stated above.

BRIEF DESCRIPTION OF THE DRAWINGS

Preferred embodiments of the invention are described below with reference to the drawings that are only provided for illustrative purposes and are not to be interpreted as being limiting. The drawings show the following.

DESCRIPTION OF PREFERRED EMBODIMENTS

Figure 1:
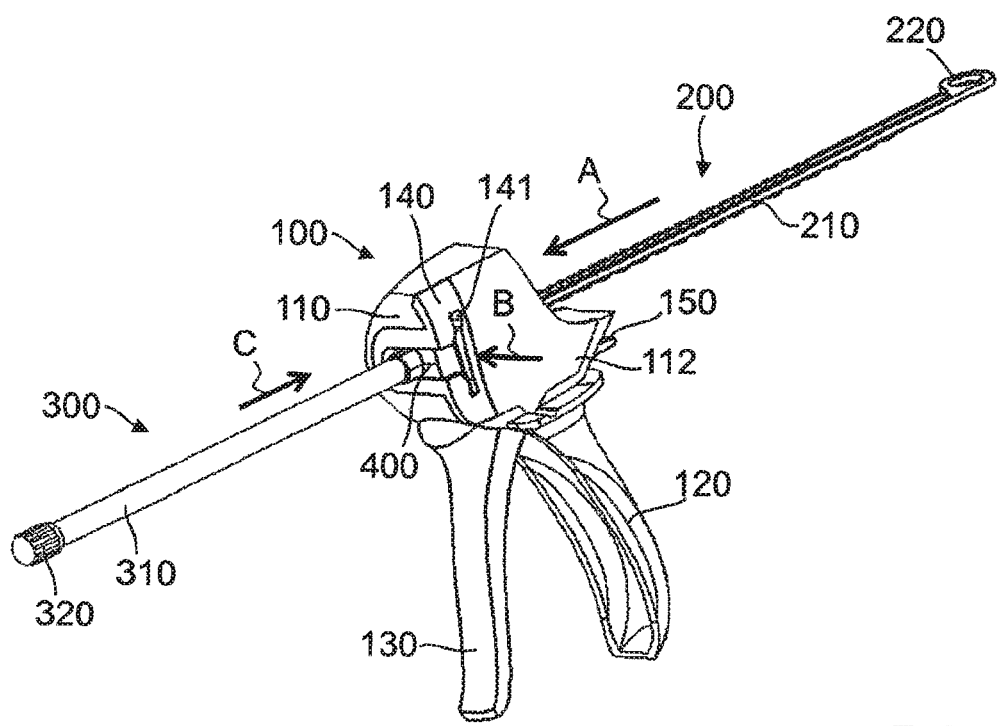
FIG. 1 an isometric view of a preferred exemplary embodiment of a discharge device according to the invention with a connected container.
Figure 2:
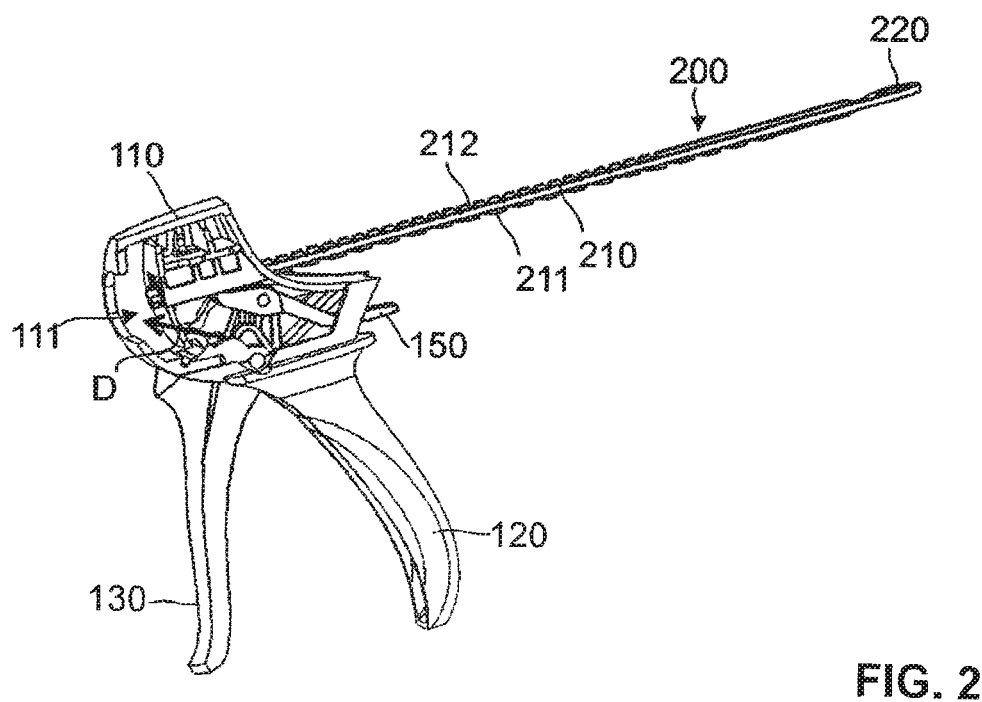
FIG. 2 a partial view of the discharge device of FIG. 1 without a container, without an adapter, without a retaining element, and without a cover.

FIGS. 1-4 illustrate different views of a discharge device 100 in the form of a dispenser gun. The device comprises a base body 110 on which a rigid handgrip 120 is formed in a single piece. An operating lever 130 is pivotably connected to the base body 110. By way of a mechanism (not shown in detail) the operating lever 130 is coupled to a piston rod 200 that extends through the base body 110. By way of operation of the operating lever 130 the piston rod 200 is slidable along a distal feed direction A relative to the base body 110. To this effect the underside of the piston rod comprises a multitude of teeth 211 (see FIG. 2). The mechanism in question can, for example, be designed according to U.S. Pat. No. 5,992,694. A backstop prevents any unintended withdrawal of the piston rod contrary to the feed direction A. This backstop can be deactivated by operating a release lever 150.

A retaining element 140 is laterally slid, along a fastening direction D, into a fastening opening 111 in the housing of the base body 110 (see FIG. 2) where it is fixed by a cover 112 (see FIG. 1). The retaining element 140 is designed as a separate replacement part and, depending on the concrete requirements, can easily be replaced during production or, if the retaining element is removably attached, subsequently by a retaining element shaped in some other manner, without the mechanism of the device needing to be changed. The retaining element defines a laterally open insertion opening 141. Said insertion opening 141 comprises two opposite slits 142, 143 that extend downwards or upwards, i.e. across the feed direction A and across the fastening direction D. In a central region between these slits the insertion opening is also open in the distal direction.

In this respect the design of the discharge device largely corresponds to the design of the discharge apparatus of US 2007/0289998 whose content is incorporated in this document by reference, to the extent that in that document the basic design of the discharge apparatus shown in FIGS. 1-4 is disclosed.

The distal end of the piston rod 200 comprises a piston 230; the proximal end comprises a flat handgrip 220. In between, the also flat main section 210 of the piston rod extends. The proximal end of the piston rod 200 can be inserted, axially contrary to the feed direction A, into the device through the insertion opening 141 while the release lever 150 is pushed. When the piston rod 200 is withdrawn, the piston 230 forms an end stop beyond which it is not possible to pull back the piston rod any further.

Figure 3:
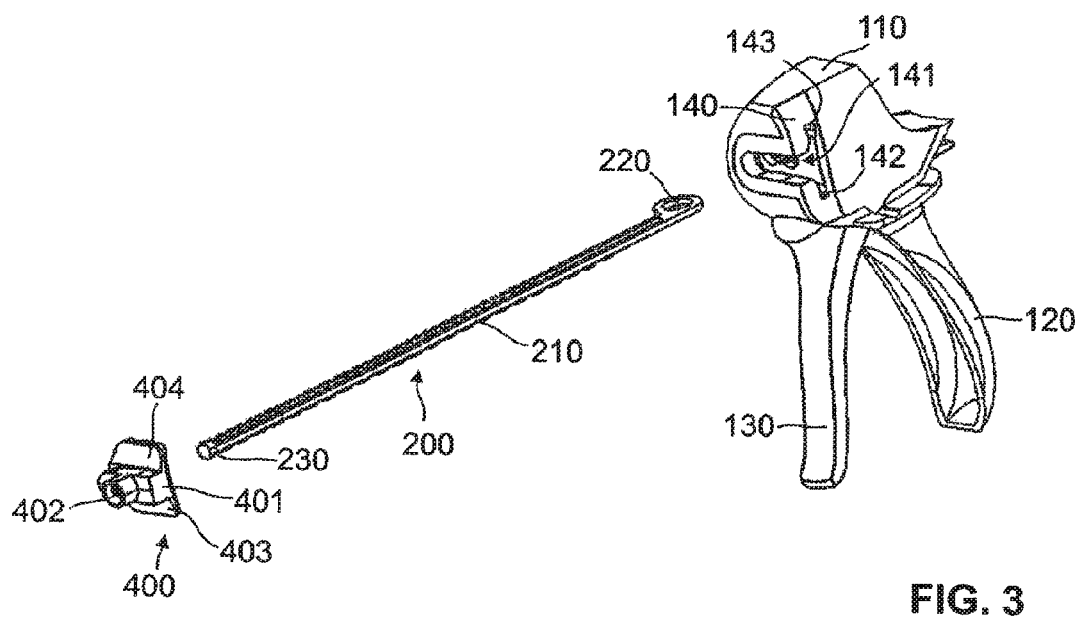
FIG. 3 an exploded view of the discharge device of FIG. 1 without a container.

Along a direction of insertion B laterally an adapter 400 is inserted into the insertion opening 141, which adapter 400 is particularly clearly shown in FIG. 3. The direction of insertion B extends along a direction that extends across the plane defined by the handgrip 120 and the lever 130, and which plane also intersects the piston rod 200 along its entire length. In the present example the direction of insertion at the same time corresponds to the direction of fastening D, along which the retaining element 140 is slid into the housing of the base body 110; however, in other embodiments of the retaining element 140 said direction of insertion can also be selected so as to differ from the above.

In its outer shape the adapter 400 approximately corresponds to the rear end of the dual syringe of US 2007/0289998. Said adapter 400 comprises a substantially cuboid main section 401 through which a passage opening for insertion of the piston rod 200 leads. In the axial distal direction a ring-shaped fastening structure 402 follows on from the main section, which fastening structure 402 radially encompasses the passage opening, and on whose interior an internal thread is formed. From the main section two retaining wings 403, 404 extend downwards and upwards, respectively, in other words laterally, i.e. across the axial direction.

The shape of the adapter 400 has been selected so as to be complementary to the shape of the insertion opening 141. Consequently the adapter 400 can easily be inserted laterally in the insertion opening 141 instead of a dual syringe. In this arrangement the piston rod 200 can remain in the device; it merely needs to be withdrawn in the proximal direction to its end stop. Mounting or replacing the adapter can thus take place very easily.

Figure 5:
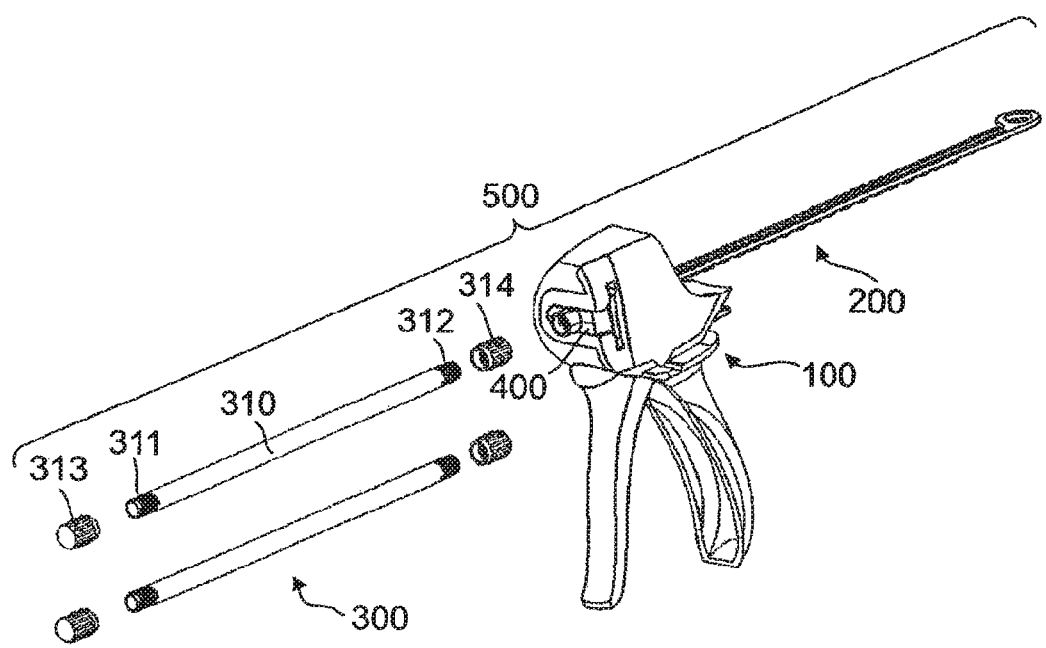
FIG. 5 a kit comprising the discharge device of FIG. 1 and several associated containers.

A container 300 is screwed into the fastening structure 402 of the adapter 400, which container 300 is shown in more detail in FIG. 5. The container has the shape of a straight cylindrical pipe 310. In the interior the pipe has a cylindrical cross section that does not substantially change along its entire length and that, in particular, also does not taper off at the ends of the pipe. The pipe 310 comprises a viscous implantable material, e.g. a synthetic bone graft substitute material or a cement. On both ends the pipe comprises identical external threads 311, 312. Prior to the pipe being inserted into the discharge device both ends of the pipe are closed by means of identical closure caps 313, 314 that comprise an internal thread and by means of it are screwed onto the external threads 311, 312. In this arrangement no separate displaceable piston is accommodated in the container 300.

Figure 4:
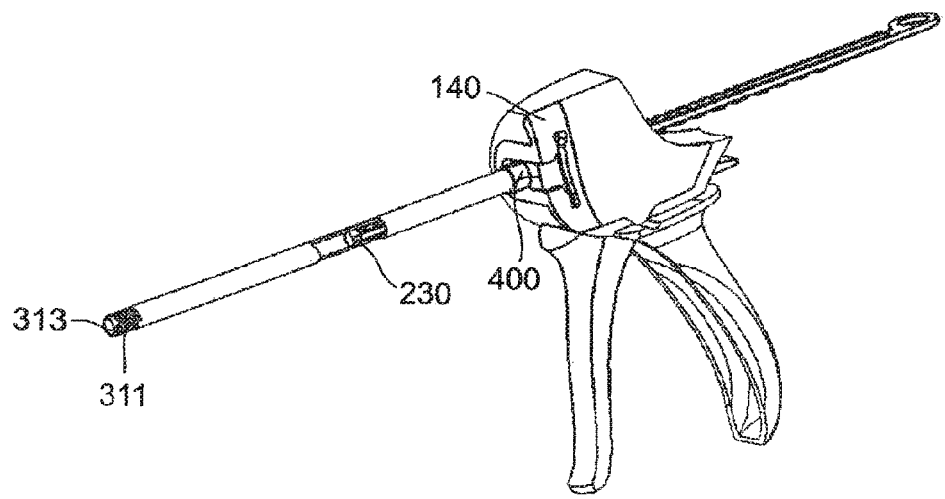
FIG. 4 a view of the discharge device of FIG. 1 with a connected container in which the container is shown so as to be partially transparent.

The device is operated as follows: prior to insertion of the pipe 310 into the device, the closure caps 313, 314 are removed by the surgeon. The pipe 310 is then inserted into the fastening structure 402 along a proximal direction C that is contrary to the feed direction A, and by means of its external thread 311 or 312 said pipe 310 is screwed into said fastening structure 402. In this process the orientation of the pipe is unimportant, in other words it does not matter whether the pipe is screwed in by the end on which the thread 311 is located or by the end on which the thread 312 is located. This makes it easy for the surgeon to handle the container. Subsequently the surgeon takes the device by its handgrip 120 and pulls the operating lever 130 with the fingers of the same hand towards the handgrip 120. Consequently the piston rod 200 is advanced along the feed direction A, and the piston 230 moves into the interior of the pipe 310. In this arrangement the dimensions of the piston 230 are selected such that the piston 230 rests on the inside against the wall of the pipe 310 so as to provide a tight seal. Consequently the piston presses the material located in the pipe in the distal direction and discharges it. FIG. 4 illustrates the device in a position in which the piston has been advanced by nearly half the length of the pipe.

The device together with one or several containers 300 can be sold as a set. FIG. 5 illustrates such a set 500 with two identical containers 300.

Figure 6:
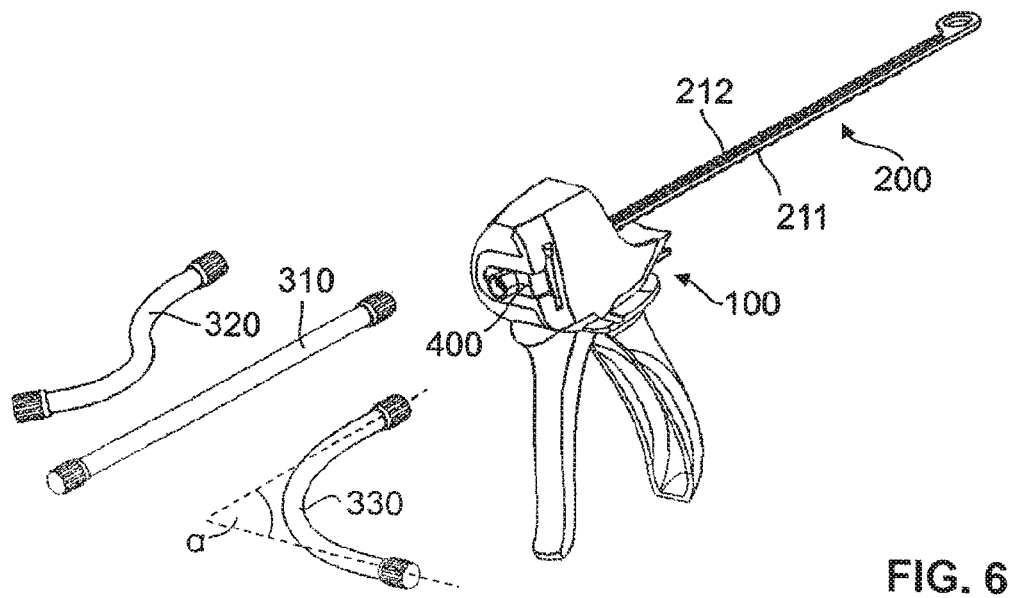
FIG. 6 the discharge device of FIG. 1 together with variously shaped containers.

FIG. 6 illustrates containers of different shapes. While one of the containers has the shape of a straight pipe 310 as was the case previously, the other containers have the shape of a curved pipe 320, 330. In this arrangement the directions defined by the ends of the pipe encompass an angle α that can easily be 45° or more; in the present example the angle α of the pipe 330 is approximately 90°. With such curved pipes it is possible to reach positions that would not otherwise be easily accessible. Instead of being rigidly curved the pipe can be flexible. To make it possible for the piston rod 200 to follow the curvature of the pipes 320, 330, the piston rod is designed so as to be particularly flexible. To this effect it comprises a multitude of incisions 212 at its top, opposite to the teeth 211, on which incisions 212 the thickness of the material is correspondingly reduced.

Figure 7:
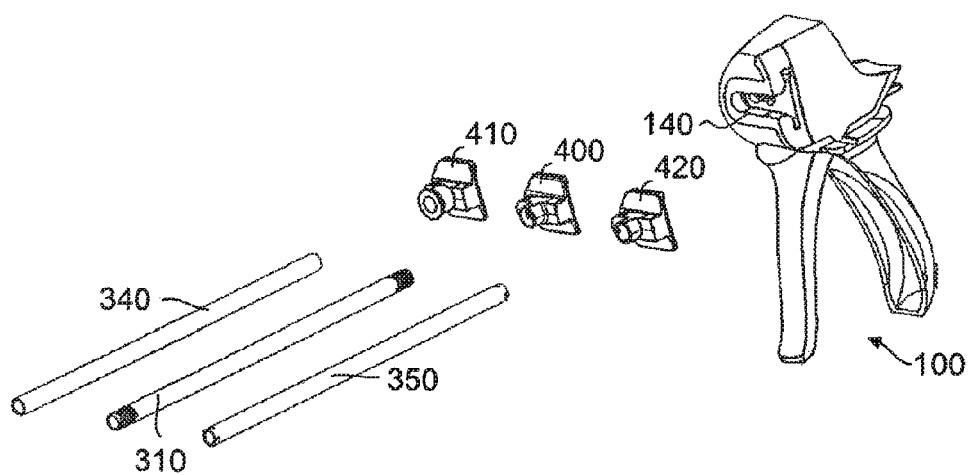
FIG. 7 the discharge device of FIG. 1 together with various types of containers.

FIG. 7 illustrates different types of container connections and corresponding adapters. Instead of providing a screw connection as is the case with pipe 310 and adapter 400 it is also possible to provide a pure plug-type connection (pipe 340 with adapter 410) or a bayonet connection (pipe 350 with adapter 420). An axial snap-lock connection is also possible. Because an adapter can easily be exchanged for another adapter such different types of fastening arrangements can easily be implemented without there being a need to alter the mechanism of the delivery device. Consequently the base body 110 with the entire mechanism can always be produced so as to be identical, independently of the type of the container to be connected, which keeps production costs to a minimum.

While, above, the invention has been described primarily with reference to a particular medical example of use, the invention is in no way limited to this. It is imaginable to use the invention also in completely other areas of application, among them also non-medical areas of application, in which a viscous material is to be discharged.

The invention claimed is:

1. A discharge device comprising:
 a base body;
 an operating lever that is manually movable relative to the base body;
  a piston rod that is slidable relative to the base body, the piston rod being coupled to the operating lever in such a manner that operation of the operating lever causes the piston rod to advance in a distal feed direction; and
 an adapter that is formed separately from the base body and is attached to the base body,
 wherein the adapter is configured to be inserted into the base body along a direction of insertion that extends across the distal feed direction, and
 wherein the adapter comprises a fastening structure configured for removable attachment of a container such that attachment of the container to the adapter takes place substantially along a proximal direction contrary to the distal feed direction when the adapter is attached to the base body.

2. The discharge device according to claim 1, wherein the operating lever is manually pivotable relative to the base body.

3. The discharge device according to claim 2, wherein the adapter comprises:
 a main section with a passage opening for the piston rod;
 a fastening structure on the main section for the container; and
 two opposing retaining wings extending in opposite lateral directions, and
 wherein the base body comprises an insertion opening, which is complementary to the adapter, with two opposite slits that extend across the feed direction and across the direction of insertion, for accommodating the retaining wings.

4. The discharge device according to claim 1,
 wherein the base body comprises a housing and a separately manufactured retaining element connected to the housing, and
 wherein the adapter is removably attached to the retaining element.

5. The discharge device according to claim 4, wherein the retaining element is configured to be slid into the housing along a fastening direction that extends across the distal feed direction.

6. The discharge device according to claim 1, wherein the adapter is removable from the base body while the piston rod is held on the base body.

7. The discharge device according to claim 1, wherein the adapter comprises a screw connection or bayonet connection, which is open in the distal feed direction, for the container.

8. The discharge device according to claim 1, wherein the piston rod is flexible such that its distal end is pivotable along at least one bending direction by an angle of at least 45° relative to its proximal end.

9. The discharge device according to claim 8, wherein the piston rod comprises a first side on which there is a plurality of teeth,
 wherein the operating lever when operated exerts a feed force directly or indirectly on the teeth in order to cause advancing of the piston rod, and
 wherein the piston rod at least on a second side, which is opposite to the first side, comprises a plurality of incisions in order to increase flexibility of the piston rod.

10. The discharge device according to claim 1, further comprising a container in the form of a cylindrical pipe with a proximal end and a distal end, the container comprising, at at least one of its ends, an external connecting structure for connection to the adapter, the connecting structure being complementary to the fastening structure of the adapter.

11. The discharge device according to claim 10, wherein the container comprises identical connection structures at the proximal end and the distal end.

12. The discharge device according to claim 10, wherein the connecting structure is an external thread.

13. The discharge device according to claim 10, wherein the container has a constant cross-sectional area along its entire length.

14. The discharge device according to claim 10, wherein the container contains a viscous material.

15. The discharge device according to claim 10, wherein the container has a length of at least 100 mm and an interior diameter between 3 and 10 mm.

16. The discharge device according to claim 10, wherein the container has a length and an interior diameter, the length being at least ten times the interior diameter.

17. The discharge device according to claim 10, wherein the container has the shape of a curved pipe.

18. The discharge device according to claim 10, wherein the container is flexible to such an extent that its distal end is pivotable by at least 45° relative to the proximal end.

\* \* \* \* \*